US006540686B2

(12) United States Patent
Heikkilä et al.

(10) Patent No.: US 6,540,686 B2
(45) Date of Patent: Apr. 1, 2003

(54) MEASUREMENT RELATING TO HUMAN BODY (75) Inventors: Ilkka Heikkilä, Oulu (FI); Seppo Nissilä, Oulu (FI)

(73) Assignee: Polar Electro Oy, Kempele (FI)

( * ) Notice: Subject to any disclaimer, the term of this patent is extended or adjusted under 35 U.S.C. 154(b) by 102 days.

(21) Appl. No.: 09/789,868

(22) Filed: Feb. 21, 2001

(65) Prior Publication Data

US 2001/0016689 A1 Aug. 23, 2001

(30) Foreign Application Priority Data

Feb. 23, 2000 (FI) ............................................. 2000416

(51) Int. Cl.$^7$ .............................. A61B 5/02; A61B 5/00
(52) U.S. Cl. ..................... 600/483; 600/301; 128/925
(58) Field of Search .................... 600/483, 481, 600/484, 485, 486, 490, 500, 508, 509, 300, 301; 128/897, 898, 925, 920, 923, 924

(56) References Cited

U.S. PATENT DOCUMENTS

| | | | | |
|---|---|---|---|---|
| 4,312,358 A | * | 1/1982 | Barney ..................... | 235/91 H |
| 4,367,752 A | | 1/1983 | Jimenez et al. | |
| 4,566,461 A | | 1/1986 | Lubell et al. | |
| 5,251,626 A | | 10/1993 | Nickolls et al. | |
| 5,263,491 A | | 11/1993 | Thornton | |
| 5,280,792 A | | 1/1994 | Leong et al. | |
| 5,620,003 A | | 4/1997 | Sepponen | |
| 5,810,722 A | * | 9/1998 | Heikkila ..................... | 600/300 |
| 5,853,351 A | | 12/1998 | Maruo et al. | |
| 6,030,342 A | * | 2/2000 | Amano et al. ............... | 600/301 |
| 6,135,951 A | * | 10/2000 | Richardson et al. .......... | 482/8 |
| 6,273,856 B1 | * | 8/2001 | Sun et al. ..................... | 482/8 |

FOREIGN PATENT DOCUMENTS

| | | |
|---|---|---|
| DE | 39 20 526 A1 | 1/1991 |
| DE | 39 22 026 A1 | 1/1991 |
| DE | 43 07 545 A1 | 9/1994 |
| EP | 0 650 742 A1 | 3/1995 |
| EP | 0 845 241 A1 | 6/1998 |
| JP | 8052119 | 2/1996 |
| JP | 10118052 | 12/1998 |
| WO | 92/03094 | 3/1992 |
| WO | 97/33512 | 9/1997 |

OTHER PUBLICATIONS

Author: Hastings et al.; Title: A Self–Organising Fuzzy Estimator For Hypoglycaemia Monitoring In Diabetic Patients, pp. 1371–1374; Date of Publication: Unknown; Place of Publication: United States.

Author: Ghevondian et al.; Title: "Modelling of Blood Glucose Profiles Non–Invasively Using A Neural Network Algorithm," p. 928; Date of Publication: Unknown; Place of Publication: United States.

* cited by examiner

Primary Examiner—Max F. Hindenburg
Assistant Examiner—Navin Natnithithadha
(74) Attorney, Agent, or Firm—Hoffmann & Baron, LLP (57) ABSTRACT A heart rate measurement arrangement wherein the heart rate measurement arrangement comprises a calculating unit comprising a mathematical model arranged to form a person's energy metabolism level as an output parameter of the model using as input parameters of the model one or more heart rate parameters and one or more physiological parameters each describing a physiological characteristic of the person, the heart rate measurement arrangement further comprising display means for displaying information formed in the calculating unit.

49 Claims, 5 Drawing Sheets

MEASUREMENT RELATING TO HUMAN BODY

FIELD OF THE INVENTION

The invention relates to health care and sports, particularly to applications which aim to determine variables relating to human energy metabolism and/or glucose content in a human body.

BACKGROUND OF THE INVENTION

The human energy economics mainly comprises carbohydrates, fats and proteins. How these are used and proportioned depends on bodily condition, the amount of nutrients in use and the intensity of exercise to be performed. The bodily condition can be studied e.g. through activity, temperature and blood pressure. The exercise stress intensity, in turn, can be measured e.g. as a heart rate frequency with respect to time, which gives a temporary, rough estimate of the exercise stress. In connection with various diseases, such as diabetes, it is important to determine the bodily energy balance and glucose content in order to find suitable treatment. Furthermore, the effect of exercise stress level in athletes on the energy balance and energy metabolism is important as regards planning a suitable diet.

The known methods for determining energy metabolism levels are based on measuring the heart rate during an exercise. Energy consumption has been estimated e.g. by an equation according to Formula (1):

$$EE=a+b*HR, \text{ wherein} \tag{1}$$

EE describes the level of energy consumption, a and b are constants by which the linear dependency between heart rate HR and EE is determined. The known method has serious disadvantages. Energy consumption calculated by the method according to Formula (1) does not take any previous cumulative exercise stress nor the quality thereof into account. The linear model is used because the energy consumption measurements being currently used are mainly based on laboratory measurements during ascending exercise stress or using constant exercise stress at a certain work load.

BRIEF DESCRIPTION OF THE INVENTION

An object of the invention is to provide an improved method for determining human energy metabolism. A further object of the invention is to provide an improved method for estimating a glucose content in a human body. This is achieved by a method disclosed in the following. The method is a method for measuring human energy metabolism, in which method information on a person's heart rate is measured in the form of one or more heart rate parameters. The method comprises forming, by means of a mathematical model modelling human metabolism, the person's energy metabolism level as an output parameter of the model using as input parameters of the model said one or more heart rate parameters and one or more physiological parameters each describing a physiological characteristic of the person, and using the output parameter of the model for estimating the person's energy metabolism.

The invention also relates to a method for measuring the amount of glucose in a human body, in which method information on a person's heart rate is measured in the form of one or more heart rate parameters. The method comprises supplying one or more heart rate parameters and one or more physiological parameters describing a physiological characteristic of the person as input parameters into a mathematical model modelling human glucose consumption, by means of which input parameters one or more of the following are formed as an output parameter of the model: the person's glucose content level, amount of glucose left in the person's body, which said one or more output parameters are used for estimating the amount of glucose used and/or the amount of glucose left in the body.

The invention also relates to a heart rate measurement arrangement comprising a calculating unit comprising a mathematical model arranged to form a person's energy metabolism level as an output parameter of the model using as input parameters of the model one or more heart rate parameters and one or more physiological parameters each describing a physiological characteristic of the person, the heart rate measurement arrangement further comprising display means for displaying information formed in the calculating unit.

The invention also relates to a heart rate measurement arrangement comprising a calculating unit comprising a mathematical model arranged to form, using as input parameters of the model one or more heart rate parameters and one or more physiological parameters each describing a physiological characteristic of a person, one or more of the following as an output parameter of the model: the person's glucose content level, amount of glucose left in the person's body, which heart rate measurement arrangement further comprises display means for displaying information formed in the calculating unit.

Preferred embodiments of the invention are disclosed in the dependent claims.

The invention thus relates to a method and apparatus for measuring human energy metabolism. The method of the invention is preferably implemented by a mathematical model which is based on the physiological facts of the human energy metabolism. In connection with the description of the invention, a mathematical model refers to a set of mathematical procedures and rules that are employed to form output parameter values from input parameter values. The mathematical procedures include arithmetic operations, such as adding, subtracting and multiplying. The mathematical model may of course also be implemented as a table or a database, in which case an output parameter value corresponding to a particular input parameter is read directly from the database. In an embodiment of the invention, the level of energy metabolism, i.e. the amount of energy consumed, is given as output variables of the mathematical model. Energy consumption can be determined as energy/time unit, i.e. kcal/min. In a preferred embodiment of the invention, the quality of energy metabolism, which means that the energy used is divided into different forms of energy, such as carbohydrates, fats and proteins, is given as output parameters of the model. In a preferred embodiment of the invention, the amount of energy left in the body is given as an output variable. In an embodiment, the quality of the remaining energy divided into different energy components is given as an output parameter. More than one output parameter of the output parameters disclosed above may also be simultaneously given as an output parameter of the model.

The mathematical model according to an embodiment of the invention returns as its output parameter one or more of the following: the glucose used by the body or the amount of glucose left in the person's body.

The set of input parameters of both the model modelling energy metabolism and the model modelling glucose consumption may vary greatly. In the solution of the invention, at least one or more heart rate parameters to be measured from heart rate information are introduced as input parameters into the model. A heart rate parameter may be e.g. heart rate, standard deviation of the heart rate, rate of change of the heart rate or other such variable measurable from heart beats. Furthermore, at least one physiological parameter describing the physiology of the user is introduced as input information into the model. The physiological parameters include height, weight, age and sex. The model can be made more accurate by using one or more optional parameters as input parameters of the model. In a preferred model, the amount of energy supplied to the body is introduced as an input parameter into the model. The amount of supplied energy refers to energy that has been consumed by eating or drinking or administered e.g. through an injection. In a preferred embodiment, the amount of energy supplied to the body can be divided into carbohydrates, fats and proteins according to the energy quality. An optional input parameter is body temperature, which can be measured e.g. from the skin by a thermometer. Furthermore, an optional input parameter of the model is the surrounding temperature, which affects the metabolism level in the same way as the body's own temperature, i.e. the higher the temperature, the higher the metabolism level. The model may also use a person's blood pressure as an input parameter, the blood pressure affecting the metabolism such that high blood pressure corresponds with high metabolism level. In a preferred embodiment, the model uses the amounts of respiratory gases, i.e. oxygen and carbon dioxide, as optional input parameters.

In a preferred embodiment of the invention, the above-described mathematical model is implemented as a neural network. In a neural network, the effect of each input parameter on each output parameter is found out by finding out the weighting coefficient describing the effect. The model is preferably trained by a sufficiently large amount of user data to enable the model to conclude the effect of each input parameter on each output parameter. The set of users used in the training is preferably very large, i.e. it comprises a group of hundreds or even thousands of people having physiological characteristics that provide as comprehensive a sample as possible. By supplying a user's physiological parameters into the trained neural network quite a good classification of the user in the model can be achieved. In a preferred embodiment, the results given by the model are improved by a reference exercise. The reference exercise is carried out at a known exercise stress level, enabling the exact values of some input parameters, such as the respiratory gases, to be measured. The operation of the neural network can be further improved by introducing feedback into the model, whereby the model can be further improved by utilizing the measurement results obtained.

In a solution according to a preferred embodiment of the invention, in order to measure energy metabolism and/or glucose, a person whose energy levels are to be monitored uses a heart rate monitor. A heart rate monitor is a device used in sports and medicine to measure information on a person's heart rate either from an electric impulse transmitted by the heart or from the pressure caused by a heart beat on an arterial vessel. Heart rate monitors are known e.g. to comprise an electrode belt to be arranged on a user's chest to measure the heart rate by means of two or more electrodes. The electrode belt transmits the measured heart rate information inductively as one or more magnetic pulses per heart beat e.g. to a receiver unit worn on the wrist. On account of the received magnetic pulses, the receiver unit calculates the heart rate and, if necessary, other heart rate variables, such as the moving standard deviation of the heart rate. The receiver unit, i.e. the wrist monitor, often also comprises a display for displaying heart rate information to the performer of an exercise, and an interface for the other facilities of the heart rate monitor. In the above-described situation, a heart rate monitor refers to an integrated whole comprising an electrode belt and a receiver unit. The heart rate monitor may also consist of one part only such that the display means are also located on the chest, which means that no information needs to be transmitted to a separate receiver unit. Furthermore, the heart rate monitor may consist of a mere wrist monitor to be arranged on the wrist, operating without an electrode belt arranged on the chest and measuring the heart rate information from the pressure in the vessel. In connection with the description of the invention, a heart rate measurement arrangement refers to the heart rate monitor solutions described above. The heart rate measurement arrangement also comprises solutions wherein the heart rate information is transmitted to an external computer or to an information network comprising display means, such as a display of a computer, for displaying the information measured or formed by the heart rate monitor.

The mathematical model required by the method of the invention and the other facilities required by the models are preferably implemented by software using a processor of the heart rate monitor. The models and facilities may also be implemented as ASIC, using separate logic components or the like. In a preferred embodiment of the invention, the heart rate monitor comprises supply means for supplying input parameter values, which supply means may be e.g. a keypad of the heart rate monitor, display equipment supporting the control, speech control, telecommunication gate for external control or the like. The heart rate monitor preferably also comprises display means for displaying output parameters. The output parameters may of course be transmitted to the user in other ways as well, e.g. by means of a speech controller or a telecommunication connection.

In connection with the description of the invention, a fitness exercise, or an athletic exercise, refers to a physical exercise wherein a person's heart rate level for a given time, e.g. for more than 10 minutes, exceeds a heart rate level corresponding to a rest state. An exercise may be considered to be divided e.g. into the following phases: warm-up phase, active phase and recovery phase, the exercise being preceded and followed by a state of rest. The different phases may be determined and separated e.g. on account of heart rate levels and/or exercise stress levels. A recovery phase, for instance, can then be determined as a performance level on which the heart rate level is dropped from 130 beats/minute to a rest level of 70 beats/minute. The invention is not restricted to measuring during an exercise only but the present invention is well suited to measuring during a rest state as well.

The invention provides several advantages. In comparison to the known methods, a person's bodily condition can be followed much more accurately as regards the energy metabolism and/or glucose parameters. Indirectly, this means that the energy balance in athletes and persons suffering from certain diseases can be monitored more accurately than in the known methods. Furthermore, when in use, the method and apparatus of the invention provide a non-invasive way of estimating the energy metabolism and/or amount of glucose in a body.

BRIEF DESCRIPTION OF THE DRAWINGS

In the following, the invention will be described in closer detail with reference to the accompanying drawings, in which.

DETAILED DESCRIPTION OF THE INVENTION

Figure 1:
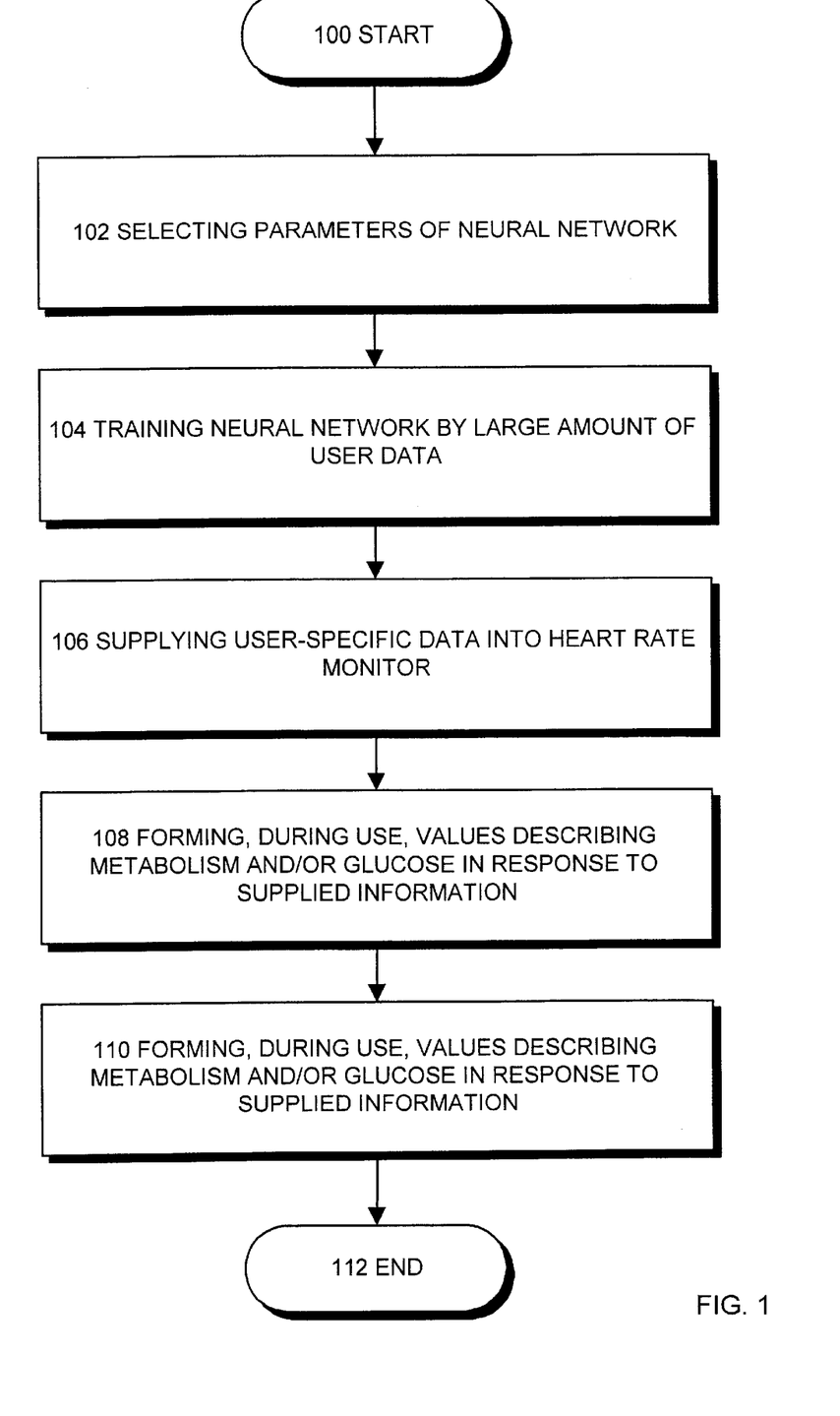
FIG. 1 shows a preferred embodiment of a method of the invention.

In the following, the invention will be described by means of preferred embodiments and with reference to accompanying FIGS. 1 to 4C. FIG. 1 describes a preferred embodiment of a method of the invention. In step 102, a mathematical model is formed in order to find one or more heart rate parameters and the effect of one or more physiological parameters on a person's metabolism level and/or the amount of glucose in the body. A heart rate parameter refers to the heart rate calculated e.g. from the heart beat frequency, standard deviation of the heart rate or such a parameter calculable from the heart beat. A physiological parameter refers to a person's age, weight, height, sex or other such parameter describing a physiological characteristic of the person. In a preferred embodiment, the mathematical model is a neural network, which is particularly well suited to complex biological modelling situations. A physiological background to the model is provided by the known physiological dependencies of metabolism that will be discussed in the following in view of the basic facts of the model.

The human energy economics mainly comprises carbohydrates, fats and proteins. How these are used and proportioned depends on the bodily condition, the amount of nutrients in use and the intensity of exercise. The carbohydrates obtained from nutrition produce glucose, which is stored as glycogen in the muscles. In glucolysis, the glucose breaks down releasing energy. The reaction may take place either aerobically or anaerobically.

Aerobic case:

glucose+$O_2$→$CO_2$+$H_2O$+energy.

Anaerobic case:

glucose→$CO_2$+$H_2O$+lactate+energy.

In addition to the breakdown of carbohydrates shown above, the breakdowns of fatty acids and protein are provided with corresponding breakdown equations; it is, however, irrelevant to shown them herein. Fatty acids can break down into energy only aerobically. In muscle, the oxidation of fatty acids requires simultaneous burning of glucose. At exercise, the muscles get the energy they need from ATP (adenosine triphosphate). An ATP deficiency formed during exercise should be replenished by producing new ATP from stored energy. At the outset of exercise, during the first 10 to 15 seconds, creatine stocks will suffice to provide energy for forming the ATP necessary for the muscles. After this, it is possible to start using the energy obtainable from the glucose in the body. Only after about 15 minutes from the outset of the exercise is it possible to utilize fatty acids. In a short-term maximal exercise lasting roughly ten to twenty seconds only energy is mainly produced anaerobically. In an exercise lasting few seconds energy is mainly produced by alactic processes by creatine phosphate. However, creatine phosphate stocks are small, and as soon as after a 10-second exercise energy production will mainly take place through lactic processes. In a longer maximal exercise lasting several minutes the proportion of aerobic energy production is increased. However, in a prolonged exercise energy is partly produced by using the same mechanisms as in a short-term exercise.

The intensity of an exercise can be studied e.g. as a heart rate frequency in regard to time. The intensity, however, only reveals a temporary intensity of the exercise. The difference between a person who is physically fit and a person who is not does not necessarily show in the intensity at which they are able to perform the exercise but first of all in the way they endure the duration of the exercise and in the way the exercise affects the person. The exercise stress level affecting the amount of cumulative metabolism is decreased by rest, so in addition to the mere intensity, a more accurate analysis of the level and quality of the metabolism would also require information on previous exercise as well. An object of the present invention is to acknowledge several different factors that are not taken into account in estimating metabolism in models based on intensity only. In an embodiment according to the model of the invention, the model can be presented by an equation according to Formula (2):

$$EE=F(HR, Act, Tem, Tair, \text{Time}, BP, Nfat, Nch), \text{wherein} \quad (2)$$

EE describes energy consumption, F refers to a function which depends on the variables in the parenthetical expression, HR describes one or more heart rate parameters, Act refers to a person's activity, Tem to the person's body temperature, Tair to the temperature of the air surrounding the body, Time to the duration of an exercise of a measurement, BP to blood pressure measured e.g. one to three times a day, Nfat to the amount of fat obtained from nutrition, and Nch to the amount of carbohydrates obtained from nutrition. The amount of glucose in the body can be estimated by using a formula corresponding to Formula (2) wherein EE is replaced by GLU to describe the amount of glucose.

In lieu of a solution based on the neural network, in an embodiment the model of Formula (2) is calibrated manually on account of measurement results. Each person calibrates the model according to the responses produced by his or her own body, e.g. the glucose content of the body can be measured from blood, whereby the parameters of the model can be calibrated appropriately.

In method step 104 of FIG. 1, the neural network is trained by a large amount of user data. The user data is preferably collected e.g. from roughly a thousand users, which enables the neural network to learn and set the weighting coefficients of the synapses such that the model gives as good results as possible. In step 106, user-specific information, such as physiological parameters and information on nutrition consumed, is supplied to the neural network. Preferably, the model is calibrated before the actual use by utilizing the real user data. As to glucose, this means that the real amount of glucose in the blood is measured in the morning using a glucose meter, the real measurement result is supplied to the model, which, using feedback, calibrates the parameters of the model such that the real measured value can be achieved. In a preferred embodiment, the mathematical model is integrated into the heart rate monitor; method step 108 shows the heart rate monitor being used. The heart rate monitor measures one or more heart rate parameters from a person's heart rate on account of which the heart rate monitor forms estimates of the variables describing energy metabolism and the amount of glucose. According to step 110, the heart rate monitor preferably displays on its display the state of energy metabolism and/or glucose content to the user of the heart rate monitor, doctor or trainer.

Figure 2:
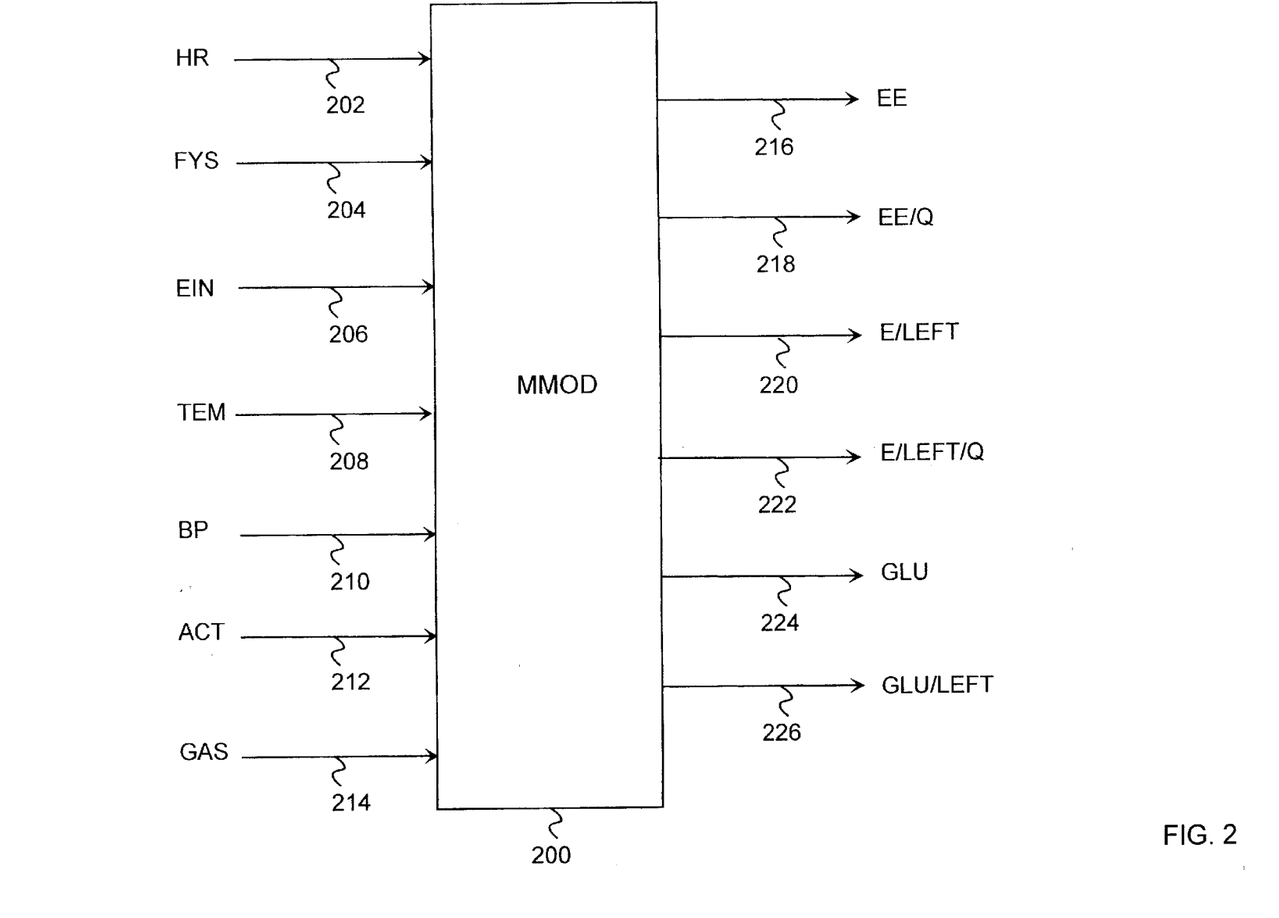
FIG. 2 is a block diagram showing the structure of a model of the invention.

FIG. 2 shows an embodiment of a mathematical model 200 mainly by means of input parameters 202 to 214 and output parameters 216 to 226 of the model 200. One or more heart rate parameters 202 calculable from a person's heart rate and one or more physiological parameters 204 of the person are introduced into the mathematical model 200, such as a neural network, as an input parameter. In an embodiment, one or more optional parameters or a set of parameters 206 to 214 are introduced into the model 200. An input parameter set 206 describes the amount of energy consumed or otherwise received by the person. In an embodiment, the amount of energy is described by one parameter. In another embodiment, the amount of energy is divided into different forms of energy, such as fats, carbohydrates and proteins, before being supplied into the model 200. An parameter set 208 describes temperatures that affect metabolism. The temperatures are described by one or more parameters, such as the temperature of the person's body or the temperature of the air surrounding the person's body. In a preferred embodiment, the person's blood pressure 210 is introduced into the model 200 as an input variable. The blood pressure can be measured e.g. one to three times a day. An activity parameter 212 describes the person's state, e.g. sleeping and being awake are preferably separated by means of the activity parameter. In a preferred embodiment, respiratory gases 214 are taken into account in calculating the energy metabolism. The respiratory gases 214 describe the amounts of inhaled oxygen and exhaled carbon dioxide. The use of the respiratory gases 214 is an accurate way to describe the energy metabolism, so it is preferable to use them e.g. when the neural network is being trained.

As output parameters, the model gives one or more of the output parameters or output parameter sets 216 to 226. shown in FIG. 2. The output parameter 216 describes the amount of energy consumption e.g. by a variable such as that of kilocalories per time unit. An output parameter set 218 describes the amount of energy consumption divided into different kinds of energy, such as fats, carbohydrates and proteins. An output parameter 220 describes the amount of energy left in the body. In a preferred embodiment, the parameters 220 describing the energy 206 consumed and the amount of energy left coexist in the model 200. A parameter set 222 describes the remaining amount of energy divided into different energy components. An output parameter 224 describes the amount of glucose used, and a parameter 226 the amount of glucose left in the body.

In a preferred embodiment, the mathematical model forms a person's exercise stress level by means of the person's one or more heart rate parameters and one or more parameters describing the strenuousness of an exercise. An exercise stress parameter may be e.g. the velocity of a runner or the resistance of an exercise bike. In determining the exercise stress, the model preferably employs one or more parameters describing the person's physical condition, such as the maximum oxygen intake capacity. The model of the embodiment is then preferably a two-step one such that an estimate of the person's exercise stress level is formed on account of the heart rate information and the parameters describing the person's energy metabolism are estimated on account of the exercise stress level.

Figure 3A:
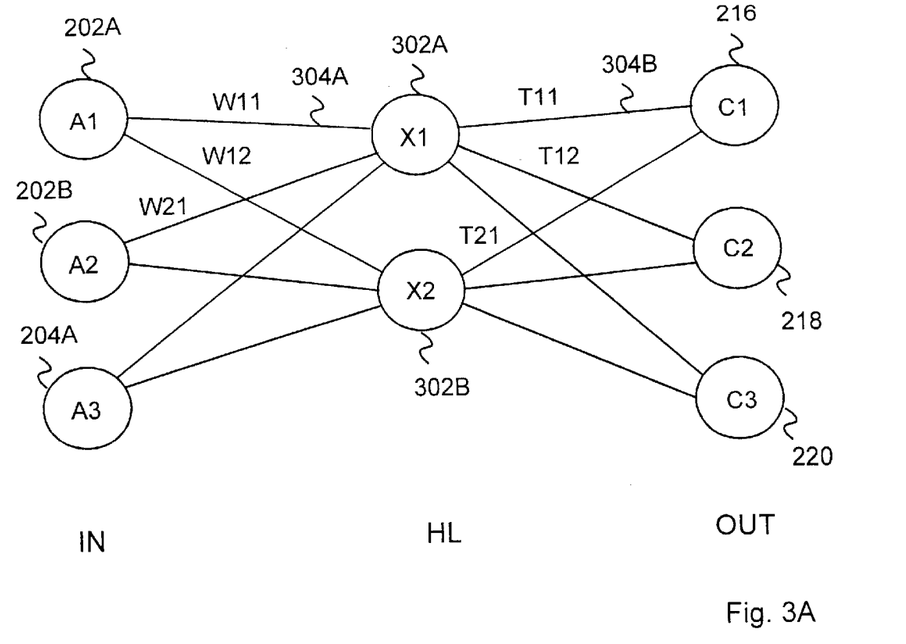
FIG. 3A shows the structure of a neural network model.
Figure 3B:
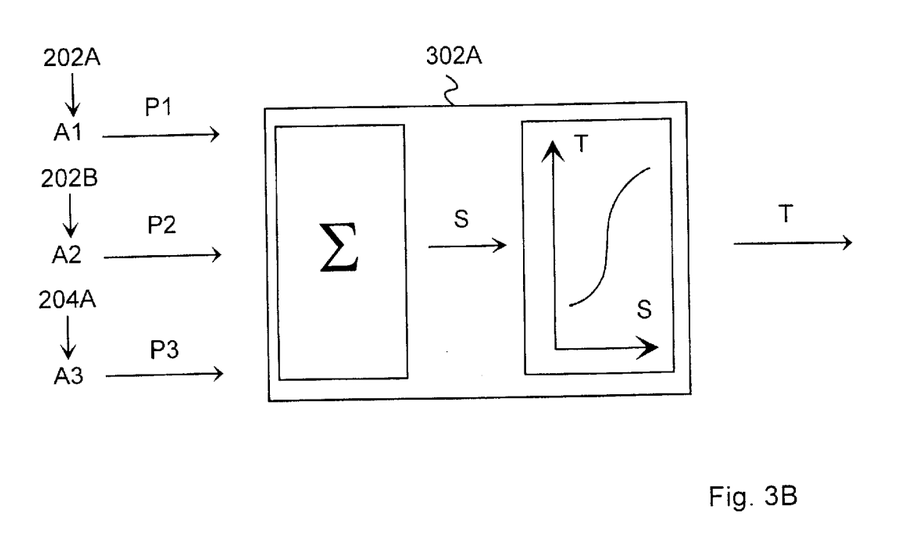
FIG. 3B shows the operation of the neural network model.

In an embodiment of the invention, the mathematical model implementing the method of the invention is implemented as a neural network, the operational principles of such a network being described by means of FIGS. 3A and 3B. A neural network is used for modelling highly complex applications, such as image and speech recognition, robotics applications and medical analysis applications, which are extremely difficult to express as a mathematical model. Referring to FIG. 3A, the neural network comprises neurons, e.g. 202A and 202B, 302A and 302B which are provided with a great number of dependencies therebetween, e.g. 304A and 304B. The dependencies 304A and 304B between the neurons are called synapses, and a weighting coefficient, e.g. W11, W12, is determined for each synapsis. The neurons, i.e. nodes, are able to perform simple calculations, e.g. the neuron 302A calculates a sum weighted by the weighting coefficients from the synapses of the previous layer. The neural network comprises at least an input layer comprising neurons 202A to 204A, and an output layer comprising neurons 216 to 220. Since the operation of the two-layer neural network is rather limited, the neural network preferably comprises at least one hidden layer HL comprising neurons 302A and 302B. Neurons on the same level do not have a common synapsis but a node has a synapsis with all neurons on adjacent levels to the level in question. FIG. 3B shows the structure of a single neuron 302A in closer detail. As its input the neuron 302A receives the corresponding input parameters 202A to 204A weighted by weighting coefficients P1 to P3 for which the neuron forms a weighted sum S. The neuron supplies the sum S to an activation function, which is typically a non-linear function of the sigmoid type. As its output the neuron 302A gives a terminal value T, which, supplied to the synapsis 304B is multiplied by a weighting coefficient T11 whereas supplied to the node 218, the terminal value is multiplied by weighting coefficient T12.

A central characteristic of the neural network is training. During a special training phase, the model is being presented with real input and output values that the model compares with the output values it has calculated. The model processes the difference between the real and calculated values, i.e. the error, and as a final result of the processing, the weighting coefficients of the synapses are adjusted in order to minimize the error. As a result of the training phase, the weight of significant synapses increases while the weight of less important synapses becomes extremely small.

Figure 4A:
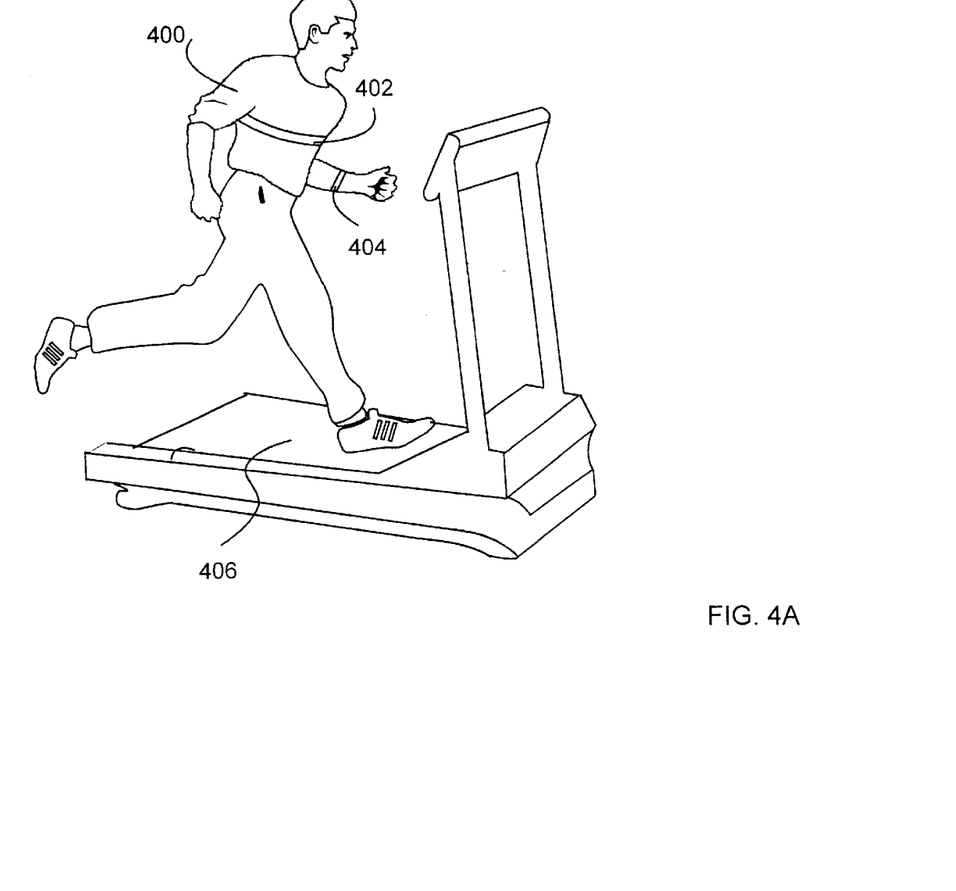
FIG. 4A shows a person performing an exercise.

FIG. 4A shows a person 400 performing an exercise on a treadmill 406. The heart rate of the person 400 is measured by a transmitter electrode belt 402 to be arranged on the chest. The heart rate is measured by two or more electrodes 410A and 410B provided in the transmitter electrode belt 402, a potential difference being formed therebetween as the heart beats. The transmitter electrode belt 402 is attached around the person's body e.g. by an elastic band made of an elastic material. The measured heart rate is transmitted preferably inductively to a receiver 404 on the wrist which preferably also comprises a display for displaying the measured heart rate. The invention is also suited to heart rate monitors wherein an electrode belt 402 on the chest is, in addition to measuring the heart rate, also responsible for storing, processing and displaying heart rate information, which means that no separate receiver unit 404 to be arranged on the wrist is needed. The heart rate monitor may also be a mere wrist device wherein the transmitter part and the receiver part are integrated into one device, in which case no transceiver nor receiver electronics is needed. The heart beat may be measured from the wrist either from an ECG signal from the arterial pressure pulse or by observing optically the changes in blood flow absorption or reflection.

Figure 4B:
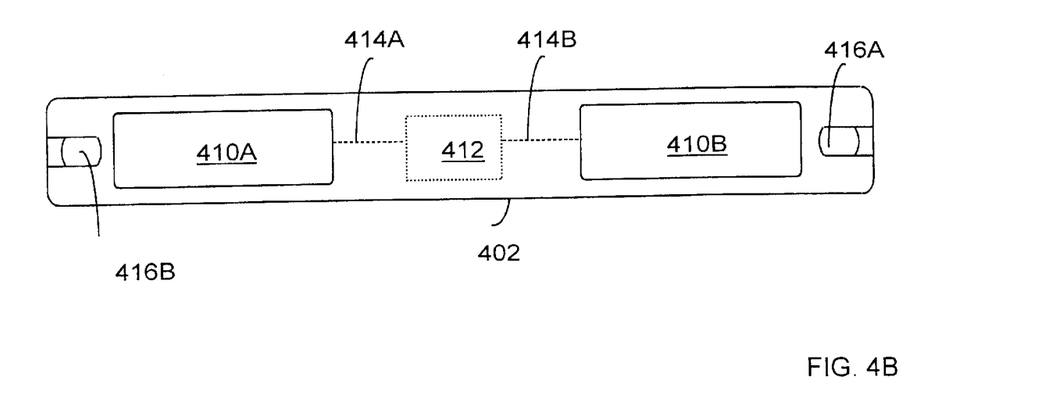
FIG. 4B shows an electrode belt according to a preferred embodiment of the invention.

FIG. 4B shows in closer detail the electrode belt 402 shown in FIG. 4A. In FIG. 4B, the electrode belt 402 is shown as seen from the side of the electrodes 410A and 410B, i.e. from the side facing the body. The figure further shows fasteners 416A and 416B by which the electrode belt 402 can be attached to the elastic band to be attached around the body. A dotted line in FIG. 4B further designates an electronics unit 412 for processing the heart rate information received from the electrodes 410A and 410B. The electrodes 410A and 410B are connected to the electronics unit 412 by connectors 414A and 414B respectively.

Figure 4C:
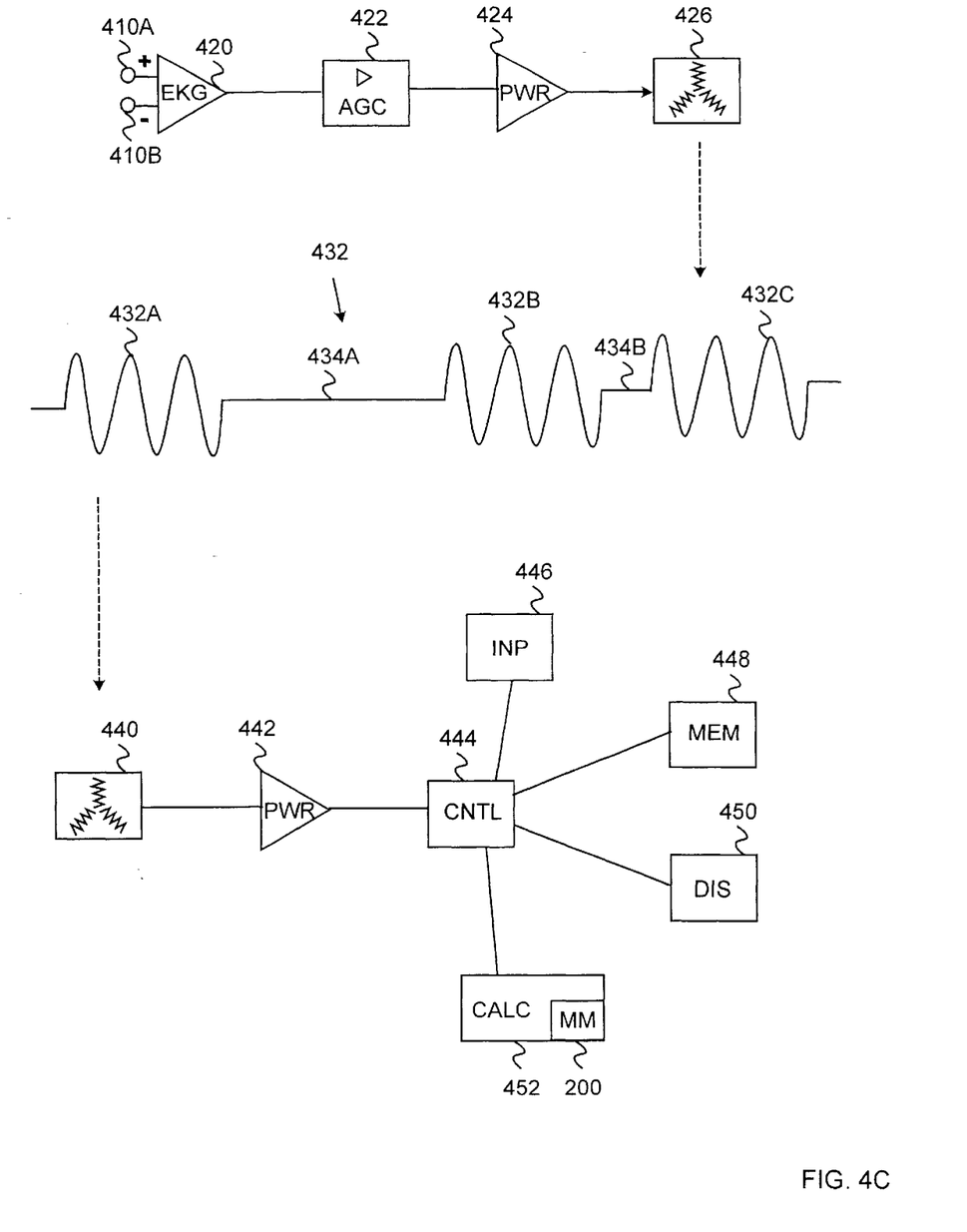
FIG. 4C shows a heart rate monitor arrangement of an embodiment of the invention.

FIG. 4C shows the structures of the transmitter electrode belt 402 and the receiver 404 by means of an embodiment. The transmitter electrode belt 402 is shown at the top of the figure, a sample of heart rate information to be transmitted in the middle of the figure, and relevant parts of the receiver unit 404 at the bottom of the figure. An electronics unit 112 of the transmitter electrode belt 402 receives the heart rate information from the means 410A and 410B for measuring one or more parameters of the heart rate information. The measuring means are preferably electrodes, and the heart rate monitor comprises at least two such electrodes; there may, however, be more of them as well. From the electrodes the signal is supplied to an ECG-preamplifier 420 wherefrom the signal is transmitted to an AGC-preamplifier 422 and, through a power amplifier 424, to a transmitter 426. The transmitter 426 is preferably implemented as a coil which inductively transmits heart rate information 430 to the receiver, such as the receiver unit 404 to be arranged on the wrist, or e.g. to an external computer.

One heart beat corresponds to e.g. one 5 kHz burst 432A, or one beat may correspond to a group 432A to 432C of several bursts. The distances between the bursts 430A to 430C and 432A and 432B may be of equal or different length, the latter case being shown in FIG. 4C. Information may be transmitted inductively or, alternatively, for instance optically or through a conductor. In an embodiment, the receiver 404, such as the receiver to be worn on the wrist, comprises a receiver coil 440 wherefrom the received signal is, via a signal receiver 442, supplied to a central processor 444, which coordinates the operation of the different parts of the receiver 404. The receiver 404 preferably also comprises a memory 448 for storing heart rate information, and display means 450 for displaying the heart rate or heart rate variables, such as the standard deviation, derived therefrom. The display means 450 are e.g. the display or speech controller of the heart rate monitor. In a preferred embodiment, the display means 450 also comprise means for transmitting heart rate or feedback information e.g. to an external computer or to an information network. The transmitting means may be implemented e.g. as an inductive coil, optic transmitter, radio transmitter or by a connector for transmission to be carried out via a connecting cable. If the information measured or formed by the heart rate monitor is transmitted to equipment external to the heart rate monitor, such as a computer, the arrangement is called a heart rate measurement arrangement. Then, according to a preferred embodiment, the display means are situated in the computer, which can be used for displaying the information stored in the memory of the heart rate monitor or measured in real time. The display means 450 may also show the user information relevant to recovering from a fitness exercise, such as the lactate content in the body, value of the sliding heart rate variation, the person's exercise stress level, duration of the recovery exercise or other such information. The display means 450 may also be used for displaying to the user the output parameters 216 to 226 of the mathematical model 200 shown in FIG. 2 relating to the energy metabolism or glucose content. The receiver 404 preferably comprises supply means 446, such as a keypad or speech control means. The supply means 446 can be used for supplying e.g. the input parameters 202 to 214 necessary for the models 200. Preferably, the one or more mathematical models 200 required by the method of the invention are implemented in a calculating unit 452 of the receiver 404. It is obvious that the calculating unit 452 does not have to be implemented as a separate device unit but the calculating unit 452 and the mathematical model 200 therein may e.g. be part of the central processor 444. Furthermore, it is obvious that the heart rate monitor does not necessarily have to comprise a calculating unit as a separate device component but the model 200 may be implemented e.g. in the central processor 444.

In the embodiment of FIG. 4C, a heart rate monitor refers to an integrated whole comprising the transmitter electrode belt 402 and the receiver 404. In an embodiment, the heart rate monitor may also be implemented such that the above-described facilities contained in the transmitter electrode belt 402 and the receiver 404 are situated in one device. The one-piece device may be either such that it is arranged on the chest for the heart rate measurement or, alternatively, the device may be used on the wrist. It is obvious to one skilled in the art that the electrode belt 402 and the receiver 404 may also comprise other parts than those shown in FIGS. 4B and 4C but it is irrelevant to describe those parts in this connection.

In a preferred embodiment, the facilities, means and one or more mathematical models implementing the above-mentioned method steps of the invention are implemented by software using a general-purpose processor. The means may also be implemented as ASIC, by separate logic components or by employing another such known method.

Although the invention has been described above with reference to the examples according to the accompanying drawings, it is obvious that the invention is not restricted thereto but can be modified in many ways within the scope of the inventive idea disclosed in the attached claims.

What is claimed is:

1. A method for measuring human energy metabolism comprising the steps of:
   measuring information on a person's heart rate, the information including one or more heart rate parameters;
   forming the person's energy metabolism level as at least one output parameter by means of a mathematical model which uses input parameters, the input parameters including one or more of the heart rate parameters and one or more physiological parameters, each of the one or more physiological parameters describing a physiological characteristic of the person, the output parameter being at least one of:
   a quality of energy metabolism;
   an amount of energy left in the body; and
   an amount of energy in the body as energy quality; and
   estimating the person's energy metabolism using the output parameter of the model.

2. A method as claimed in claim 1, wherein the output parameter of the model describing energy metabolism is formed on account of the person's exercise stress level, the exercise stress level being estimated in the model by means of the information on the person's heart rate and one or more exercise stress parameters describing the stressfulness of a fitness exercise.

3. A method as claimed in claim 1, wherein at least one of the energy metabolism quality and energy quality describe energy consumption in one or more energy components including at least one of:

carbohydrates;
fats; and
proteins.

4. A method for measuring human energy metabolism comprising the steps of:
    measuring information on a person's heart rate, the information including one or more heart rate parameters;
    forming the person's energy metabolism level as at least one output parameter by means of a mathematical model which uses input parameters, the input parameters including one or more of the heart rate parameters and one or more physiological parameters, each of the one or more physiological parameters describing a physiological characteristic of the person, the at least one output parameter describing energy metabolism formed on account of the person's exercise stress level, the exercise stress level being estimated in the model by means of the information on the person's heart rate level and one or more exercise stress parameters describing the stressfulness of a fitness exercise; and
    estimating the person's energy metabolism using the output parameter of the model.

5. A method for measuring human energy metabolism comprising the steps of:
    measuring information on a person's heart rate, the information including one or more heart rate parameters;
    forming the person's energy metabolism level as at least one output parameter by means of a mathematical model which uses input parameters, the input parameters including one or more of the heart rate parameters and one or more physiological parameters, each of the one or more physiological parameters describing a physiological characteristic of the person, the input parameters including at least one of:
        an amount of obtained energy;
        a quality of obtained energy;
        a person's activity;
        a temperature of the person's skin;
        a temperature of the air surrounding the person's body;
        a person's blood pressure;
        an exercise stress parameter describing the hardness of exercise; and
        an amount of respiratory gases; and
    estimating the person's energy metabolism using the output parameter of the model.

6. A method as claimed in claim 5, wherein the energy metabolism describe energy consumption in one or more energy components including at least one of:
    carbohydrates;
    fats; and
    proteins.

7. A method for measuring human energy metabolism comprising the steps of:
    measuring information on a person's heart rate, the information including one or more heart rate parameters;
    forming the person's energy metabolism level as at least one output parameter by means of a mathematical model which uses input parameters, the input parameters including one or more of the heart rate parameters and one or more physiological parameters, each of the one or more physiological parameters describing a physiological characteristic of the person; and
    estimating the person's energy metabolism using the output parameter of the model, the energy metabolism being described in one or more energy components including at least one of:
        carbohydrates;
        fats; and
        proteins.

8. A method for measuring human energy metabolism comprising the steps of:
    measuring information on a person's heart rate, the information including one or more heart rate parameters;
    forming the person's energy metabolism level as at least one output parameter by means of a mathematical model which uses input parameters, the mathematical model being a neural network and the input parameters including one or more of the heart rate parameters and one or more physiological parameters, each of the one or more physiological parameters describing a physiological characteristic of the person; and
    estimating the person's energy metabolism using the output parameter of the model.

9. A method as claimed in claim 8, wherein the model is trained on a basis of a collection of a large group of user information.

10. A method as claimed in claim 9, wherein in the training of the neural network, weighting coefficients between neurons of the neural network are calibrated by means of feedback by utilizing a value of one or more output parameters.

11. A method for measuring human energy metabolism comprising the steps of:
    measuring information on a person's heart rate, the information including one or more heart rate parameters, the heart rate parameters including at least one of:
        a heart rate describing a heart beat frequency;
        a standard deviation of the heart rate; and
        a rate of change of the heart rate;
    forming the person's energy metabolism level as at least one output parameter by means of a mathematical model which uses input parameters, the input parameters including one or more of the heart rate parameters and one or more physiological parameters, each of the one or more physiological parameters describing a physiological characteristic of the person; and
    estimating the person's energy metabolism using the output parameter of the model.

12. A method for measuring human energy metabolism comprising the steps of:
    measuring information on a person's heart rate, the information including one or more heart rate parameters; the information on the person's heart rate being measured by a heart rate monitor;
    forming the person's energy metabolism level as at least one output parameter by means of a mathematical model which uses input parameters, the input parameters including one or more of the heart rate parameters and one or more physiological parameters, each of the one or more physiological parameters describing a physiological characteristic of the person; and
    estimating the person's energy metabolism using the output parameter of the model.

13. A method for measuring human energy metabolism comprising the steps of:
    measuring information on a person's heart rate, the information including one or more heart rate parameters;
    forming the person's energy metabolism level as at least one output parameter by means of a mathematical model contained in a heart rate monitor which uses input parameters, the input parameters including one or more of the heart rate parameters and one or more physiological parameters, each of the one or more physiological parameters describing a physiological characteristic of the person; and estimating the person's energy metabolism using the output parameter of the model.

14. A method for measuring human energy metabolism comprising the steps of:

measuring information on a person's heart rate, the information including one or more heart rate parameters;

forming the person's energy metabolism level as at least one output parameter by means of a mathematical model which uses input parameters, the input parameters including one or more of the heart rate parameters and one or more physiological parameters, each of the one or more physiological parameters describing a physiological characteristic of the person, the output parameter being readable from a display of a heart rate monitor; and estimating the person's energy metabolism using the output parameter of the model.

15. A method for measuring the amount of glucose in a human body comprising the steps of:

measuring information on a person's heart rate, the information including one or more heart rate parameters;

forming at least one of the person's glucose content level and an amount of glucose left in the person's body as at least one output parameter by means of a mathematical model for modelling human glucose consumption which uses input parameters, the input parameters including one or more of the heart rate parameters and one or more physiological parameters, each of the one or more physiological parameters describing a physiological characteristic of the person, the output parameter being formed on account of the person's exercise stress level, the exercise stress level being estimated in the model by means of the information on the person's heart rate and one or more exercise stress parameters which describe a stressfulness of a fitness exercise; and estimating at least one of an amount of glucose used and the amount of glucose left in the body using the output parameter of the model.

16. A method as claimed in claim 15, wherein the glucose consumption is described in one or more energy components including at least one of:

carbohydrates;

fats; and proteins.

17. A method for measuring the amount of glucose in a human body comprising the steps of:

measuring information on a person's heart rate, the information including one or more heart rate parameters;

forming at least one of the person's glucose content level and an amount of glucose left in the person's body as at least one output parameter by means of a mathematical model for modelling human glucose consumption which uses input parameters, the input parameters including one or more of the heart rate parameters and one or more physiological parameters, each of the one or more physiological parameters describing a physiological characteristic of the person, the input parameters including at least one of:

an amount of obtained energy;

a quality of obtained energy;

a person's activity;

a temperature of the person's skin;

a temperature of the air surrounding the person's body;

a person's blood pressure;

an exercise stress parameter describing the hardness of exercise; and an amount of respiratory gases; and estimating at least one of an amount of glucose used and the amount of glucose left in the body using the output parameter of the model.

18. A method as claimed in claim 17, wherein the glucose consumption is described in one or more energy components including at least one of:

carbohydrates;

fats; and proteins.

19. A method for measuring the amount of glucose in a human body comprising the steps of:

measuring information on a person's heart rate, the information including one or more heart rate parameters;

forming at least one of the person's glucose content level and an amount of glucose left in the person's body as at least one output parameter by means of a mathematical model for modelling human glucose consumption which uses input parameters, the input parameters including one or more of the heart rate parameters and one or more physiological parameters, each of the one or more physiological parameters describing a physiological characteristic of the person, the glucose consumption is described in one or more energy components including at least one of:

carbohydrates;

fats; and proteins; and estimating at least one of an amount of glucose used and the amount of glucose left in the body using the output parameter of the model.

20. A method for measuring the amount of glucose in a human body comprising the steps of:

measuring information on a person's heart rate, the information including one or more heart rate parameters;

forming at least one of the person's glucose content level and an amount of glucose left in the person's body as at least one output parameter by means of a mathematical model for modelling human glucose consumption which uses input parameters, the mathematical model being a neural network and the input parameters including one or more of the heart rate parameters and one or more physiological parameters, each of the one or more physiological parameters describing a physiological characteristic of the person; and estimating at least one of an amount of glucose used and the amount of glucose left in the body using the output parameter of the model.

21. A method as claimed in claim 20, wherein the model is trained on a basis of a collection of a large group of user information.

22. A method as claimed in claim 21, wherein in the training of the neural network, weighting coefficients between neurons of the neural network are calibrated by means of feedback by utilizing a value of one or more output parameters.

23. A method for measuring the amount of glucose in a human body comprising the steps of:

measuring information on a person's heart rate, the information including one or more heart rate parameters, the heart rate parameters including at least one of:

a heart rate describing a heart beat frequency;
a standard deviation of the heart rate; and
a rate of change of the heart rate;
forming at least one of the person's glucose content level and an amount of glucose left in the person's body as at least one output parameter by means of a mathematical model for modelling human glucose consumption which uses input parameters, the input parameters including one or more of the heart rate parameters and one or more physiological parameters, each of the one or more physiological parameters describing a physiological characteristic of the person; and
estimating at least one of an amount of glucose used and the amount of glucose left in the body using the output parameter of the model.

24. A method as claimed in claim 15, wherein the one or more physiological parameters include at least one of age, sex, height, and weight.

25. A method as claimed in claim 15, wherein the information on the person's heart rate is measured by a heart rate monitor.

26. A method for measuring the amount of glucose in a human body comprising the steps of:
measuring information on a person's heart rate, the information including one or more heart rate parameters;
forming at least one of the person's glucose content level and an amount of glucose left in the person's body as at least one output parameter by means of a mathematical model for modelling human glucose consumption which uses input parameters, the mathematical model being contained in a heart rate monitor and the input parameters including one or more of the heart rate parameters and one or more physiological parameters, each of the one or more physiological parameters describing a physiological characteristic of the person; and
estimating at least one of an amount of glucose used and the amount of glucose left in the body using the output parameter of the model.

27. A method for measuring the amount of glucose in a human body comprising the steps of:
measuring information on a person's heart rate, the information including one or more heart rate parameters;
forming at least one of the person's glucose content level and an amount of glucose left in the person's body as at least one output parameter by means of a mathematical model for modelling human glucose consumption which uses input parameters, the input parameters including one or more of the heart rate parameters and one or more physiological parameters, each of the one or more physiological parameters describing a physiological characteristic of the person, the output parameter being readable from a display of a heart rate monitor; and
estimating at least one of an amount of glucose used and the amount of glucose left in the body using the output parameter of the model.

28. A heart rate measurement arrangement comprising:
a calculating unit having a mathematical model arranged to form a person's energy metabolism level as an output parameter of the model using as input parameters of the model one or more heart rate parameters and one or more physiological parameters each describing a physiological characteristic of the person;
a display means for displaying information formed in the calculating unit;
an electrode belt for measuring heart rate, the electrode belt having a transmitter; and
a receiver unit having a receiver for receiving information transmitted from at least one of the transmitter, the calculating unit, and the display means.

29. A heart rate measurement arrangement as claimed in claim 28, wherein the display means is a display of the receiver unit.

30. A heart rate measurement arrangement comprising:
a calculating unit having a mathematical model arranged to form a person's energy metabolism level as an output parameter of the model using as input parameters of the model one or more heart rate parameters and one or more physiological parameters each describing a physiological characteristic of the person, the mathematical model being configured so that the output parameter is at least one of:
a quality of energy metabolism;
an amount of energy left in the body; and
an amount of energy in the body as energy quality; and
a display means for displaying information formed in the calculating unit.

31. A heart rate measurement arrangement as claimed in claim 30, wherein at least one of the quality of energy metabolism and the amount of energy in the body as energy quality describe energy consumption in one or more energy components including at least one of:
carbohydrates;
fats; and
proteins.

32. A heart rate measurement arrangement as claimed in claim 30, wherein the mathematical model is arranged to form the output parameter on account of the person's exercise stress level, the exercise stress level being formed in the model by means of the person's heart rate and one or more exercise stress parameters describing the stressfulness of a fitness exercise.

33. A heart rate measurement arrangement comprising:
a calculating unit having a mathematical model arranged to form a person's energy metabolism level as an output parameter of the model using as input parameters of the model one or more heart rate parameters and one or more physiological parameters each describing a physiological characteristic of the person, the output parameter being formed on account of the person's exercise stress level, the exercise stress level being formed in the model by means of the information on the person's heart rate and one or more exercise stress parameters which describe a stressfulness of a fitness exercise; and
a display means for displaying information formed in the calculating unit.

34. A heart rate measurement arrangement comprising:
a calculating unit having a mathematical model arranged to form a person's energy metabolism level as an output parameter of the model using as input parameters of the model one or more heart rate parameters and one or more physiological parameters each describing a physiological characteristic of the person; and
a display means for displaying information formed in the calculating unit,
wherein the person's energy metabolism level is described as energy consumption in at least one energy components including at least one of:

carbohydrates;
fats; and
proteins.

35. A heart rate measurement arrangement as claimed in claim wherein the input parameters including at least one of:
an amount of obtained energy;
a quality of obtained energy;
a person's activity;
a temperature of the person's skin;
a temperature of the air surrounding the person's body;
a person's blood pressure;
an exercise stress parameter describing the hardness of exercise; and
an amount of respiratory gases.

36. A heart rate measurement arrangement comprising:
a calculating unit having a mathematical model, the mathematical model being a neural network arranged to form a person's energy metabolism level as an output parameter of the model using as input parameters of the model one or more heart rate parameters and one or more physiological parameters each describing a physiological characteristic of the person; and
a display means for displaying information formed in the calculating unit.

37. A heart rate measurement arrangement as claimed in claim 36, wherein the model is trained on a basis of a collection of a large group of user information.

38. A heart rate measurement arrangement as claimed in claim 37, wherein in the training of the neural network, weighting coefficients between neurons of the neural network are calibrated by means of feedback by utilizing the value of one or more output parameters.

39. A heart rate measurement arrangement comprising:
a calculating unit having a mathematical model arranged to form a person's energy metabolism level as an output parameter of the model using as input parameters of the model one or more heart rate parameters and one or more physiological parameters each describing a physiological characteristic of the person, the heart rate parameters including at least one of:
a heart rate describing a heart beat frequency;
a standard deviation of the heart rate; and
a rate of change of the heart rate; and
a display means for displaying information formed in the calculating unit.

40. A heart rate measurement arrangement comprising:
a calculating unit having a mathematical model arranged to form at least one of a person's glucose content level and amount of glucose left in a person's body as an output parameter of the model using as input parameters of the model one or more heart rate parameters and one or more physiological parameters each describing a physiological characteristic of the person;
a display means for displaying information formed in the calculating unit;
an electrode belt for measuring heart rate, the electrode belt having a transmitter; and
a receiver unit having a receiver for receiving information transmitted from at least one of the transmitter, the calculating unit, and the display means.

41. A heart rate measurement arrangement as claimed in claim 40, wherein the electrode belt includes at least two electrodes for identifying a heart beat from an electric signal transmitted by a heart and for transmitting the measured heart rate information to the receiver unit.

42. A heart rate measurement arrangement as claimed in claim 40, wherein the display means is a display of the receiver unit.

43. A heart rate measurement arrangement as claimed in claim 41, wherein the receiver of the receiver unit is arranged to receive the information transmitted wirelessly by the transmitter of the electrode belt.

44. A heart rate measurement arrangement comprising:
a calculating unit having a mathematical model arranged to form at least one of a person's glucose content level and an amount of glucose left in a person's body as an output parameter of the model using as input parameters of the model one or more heart rate parameters and one or more physiological parameters each describing a physiological characteristic of the person, the output parameter of the model describing glucose consumption being formed on account of a person's exercise stress level, the exercise stress level being estimated in the model by means of the person's heart rate parameters and one or more exercise stress parameters which describe the stressfulness of a fitness exercise; and
a display means for displaying information formed in the calculating unit.

45. A heart rate measurement arrangement comprising:
a calculating unit having a mathematical model arranged to form at least one of a person's glucose content level and amount of glucose left in a person's body as an output parameter of the model using as input parameters of the model one or more heart rate parameters and one or more physiological parameters each describing a physiological characteristic of the person, the input parameters including at least one of:
an amount of obtained energy;
a quality of obtained energy;
a person's activity;
a temperature of the person's skin;
a temperature of the air surrounding the person's body;
a person's blood pressure;
an exercise stress parameter describing the hardness of exercise; and
an amount of respiratory gases; and
a display means for displaying information formed in the calculating unit,
wherein the output parameter is described as energy consumption in at least one energy components including at least one of:
carbohydrates;
fats; and
proteins.

46. A heart rate measurement arrangement comprising:
a calculating unit having a mathematical model, the mathematical model being a neural network arranged to form at least one of a person's glucose content level and amount of glucose left in a person's body as an output parameter of the model using as input parameters of the model one or more heart rate parameters and one or more physiological parameters each describing a physiological characteristic of the person; and
a display means for displaying information formed in the calculating unit.

47. A heart rate measurement arrangement as claimed in claim 46, wherein the model is trained on a basis of a collection of a large group of user information.

48. A heart rate measurement arrangement as claimed in claim 47, wherein in the training of the neural network, weighting coefficients between neurons of the neural network are calibrated by means of feedback by utilizing the value of one or more output parameters.

49. A heart rate measurement arrangement comprising:
a calculating unit having a mathematical model arranged to form at least one of a person's glucose content level and amount of glucose left in a person's body as an output parameter of the model using as input parameters of the model one or more heart rate parameters and one or more physiological parameters each describing a physiological characteristic of the person, the heart rate parameters including at least one of:
a heart rate describing a heart beat frequency;
a standard deviation of the heart rate; and
a rate of change of the heart rate; and
a display means for displaying information formed in the calculating unit.

* * * * *

UNITED STATES PATENT AND TRADEMARK OFFICE
CERTIFICATE OF CORRECTION

PATENT NO.   : 6,540,686 B2  
DATED        : April 1, 2003  
INVENTOR(S)  : Heikkila et al.

It is certified that error appears in the above-identified patent and that said Letters Patent is hereby corrected as shown below:

<u>Title page,</u>
Item [30], reads "February 23, 2000   (FI)………………..2000416" and should read
-- February 23, 2000  (FI)…………………...20000416 --

Signed and Sealed this

Twenty-third Day of September, 2003

JAMES E. ROGAN
*Director of the United States Patent and Trademark Office*